(12) United States Patent
Kawabe

(10) Patent No.: US 6,380,419 B2
(45) Date of Patent: Apr. 30, 2002

(54) PROCESS FOR SIMULTANEOUS PRODUCTION OF ETHYLENE GLYCOL AND CARBONATE ESTER

(75) Inventor: Kazuki Kawabe, Yokkaichi (JP)

(73) Assignee: Mitsubishi Chemical Corporation, Tokyo (JP)

(*) Notice: Subject to any disclaimer, the term of this patent is extended or adjusted under 35 U.S.C. 154(b) by 0 days.

(21) Appl. No.: 09/760,785

(22) Filed: Jan. 17, 2001

(30) Foreign Application Priority Data

Jan. 19, 2000 (JP) ........................................ 2000-009865

(51) Int. Cl.⁷ ........................... C07C 68/06; C07C 27/00
(52) U.S. Cl. ........................................ 558/277; 568/858
(58) Field of Search ........................................ 558/277

(56) References Cited

U.S. PATENT DOCUMENTS

| | | | | |
|---|---|---|---|---|
| 4,661,609 A | * | 4/1987 | Knifton | 558/277 |
| 4,734,518 A | * | 3/1988 | Knifton | 558/277 |
| 5,214,182 A | | 5/1993 | Knifton | 558/277 |
| 5,847,189 A | | 12/1998 | Tojo et al. | 558/277 |
| 6,080,897 A | | 6/2000 | Kawabe | 568/858 |
| 6,162,940 A | * | 12/2000 | Chang et al. | 558/277 |
| 6,166,240 A | * | 12/2000 | Chang et al. | 558/277 |
| 6,187,972 B1 | | 2/2001 | Kawabe et al. | 568/858 |
| 6,207,850 B1 | * | 3/2001 | Jiang et al. | 558/277 |

FOREIGN PATENT DOCUMENTS

WO    WO 99/64382    12/1999

* cited by examiner

*Primary Examiner*—Fiona T. Powers
(74) *Attorney, Agent, or Firm*—Oblon, Spivak, McClelland, Maier & Neustadt, P.C.

(57) ABSTRACT

Ethylene glycol and a carbonate ester are simultaneously produced by reacting ethylene oxide and carbon dioxide to form ethylene carbonate, hydrolyzing of the solution containing the ethylene carbonate to obtain ethylene glycol, purifying ethylene glycol, transesterifying ethylene carbonate and a hydroxyl group-containing compound to form the corresponding carbonate ester and ethylene glycol, separating the carbonate ester and separating ethylene carbonate.

5 Claims, 2 Drawing Sheets

PROCESS FOR SIMULTANEOUS PRODUCTION OF ETHYLENE GLYCOL AND CARBONATE ESTER

The present invention relates to an efficient process for simultaneously producing ethylene glycol and a carbonate ester as industrial materials, especially ethylene glycol important as a raw material for polyester resin and a carbonate ester such as dimethyl carbonate useful as a raw material for polycarbonate resin.

For production of ethylene glycol (occasionally referred to simply as "EG" hereinafter), a route via ethylene carbonate (occasionally referred to simply as "EC" hereinafter) has the advantage of giving ethylene glycol highly selectively with little production of dimers and trimers such as diethylene glycol and triethylene glycol over direct hydration of ethylene oxide and is studied extensively. The route to ethylene glycol via ethylene carbonate comprises reaction between ethylene oxide and carbon dioxide and subsequent hydrolysis of the resulting ethylene carbonate.

Meanwhile, production of a carbonate ester by transesterifying ethylene carbonate and a hydroxyl group-containing compound such as methanol is also known well.

However, these production processes are usually carried out independently in independent facilities.

The reaction between ethylene oxide and carbon dioxide for production of ethylene carbonate used by these two processes as the common starting material is slow, and it is known that addition of water is preferred to accelerate the reaction. Because addition of water also induces hydrolysis of ethylene carbonate into ethylene glycol, the reaction product has to be purified before used as the starting material for production of a carbonate ester. However, it takes laborious treatment to completely separate azeotropic ethylene carbonate and ethylene glycol.

On the other hand, in the process of producing ethylene glycol, addition of water for preparation of ethylene glycol is not problematic. However, because carbon dioxide obtained, for example, by burning hydrocarbons such as heavy oil as a precursor of ethylene carbonate is not immobilized in the product and is released from the system after the hydrolysis, there is a problem of leakage of carbon dioxide into the environment proportional to production of ethylene glycol.

Furthermore, because the transesterification involved in production of a carbonate ester is an equilibratory reaction, the reaction solution after the reaction contains unreacted ethylene carbonate. Recovery of ethylene carbonate from the remainder left behind the separation of the resulting target carbonate ester for reuse requires a separation procedure involving distillation. However, due to the presence of ethylene glycol in the reaction solution, the above-mentioned azeotropic property also comes up as a problem.

The object of the present invention is to provide a process which simplifies these two processes which involve cumbersome operations and release plenty of carbon dioxide from the system when conducted separately and reduces leakage of carbon dioxide into the environment.

As a result of the investigations to solve the above-mentioned problems, the present inventor has found out that the above-mentioned problems can be solved by combining the two processes with intervention by a step for purification of ethylene carbonate and have accomplished the present invention.

Namely, the present invention provides a process for simultaneously producing ethylene glycol and a carbonate ester comprising the following steps (a) to (c) for production of ethylene glycol, the following steps (d) and (e) for production of a carbonate ester and the following step (f) for purification of ethylene carbonate, wherein the step (f) intervenes to combine production of ethylene glycol and production of the carbonate ester:

(a) an EC formation step of reacting ethylene oxide and carbon dioxide to form a reaction solution containing ethylene carbonate, (b) a hydrolysis step of reacting the solution containing ethylene carbonate with water to give an aqueous solution containing ethylene glycol, (c) an EG purification step of purifying and collecting ethylene glycol from an aqueous solution containing ethylene glycol obtained mainly in the step (b), (d) a transesterification step of transesterifying ethylene carbonate and a hydroxyl group-containing compound to form the corresponding carbonate ester and ethylene glycol, (e) a carbonate purification step of separating the carbonate ester from the solution obtained in the step (d), and (f) an EC purification step of separating ethylene carbonate by distillation from at least part of the reaction solution obtained in the step (a) and the remainder left behind the separation of the carbonate ester in step (e), feeding the ethylene carbonate to the step (d) and feeding the remainder to the step (b).

According to another aspect of the present invention, the present invention also provides the above-mentioned process for simultaneously producing ethylene glycol and a carbonate ester wherein ethylene glycol containing ethylene carbonate is separated from the remainder left behind the separation of the carbonate ester in step (e) as the top fraction and fed to the step (b) without passing the step (f), and the remainder as the bottom fraction is returned to the step (d).

Further, according to another aspect of the present invention, the present invention also provides the above-mentioned process for simultaneously producing ethylene glycol and a carbonate ester wherein the hydroxyl group-containing compound is a monohydric or dihydric alcohol, especially methanol.

According to still another aspect of the present invention, the present invention provides the above-mentioned process for simultaneously producing ethylene glycol and a carbonate ester wherein the ethylene oxide feed to the step (a) is obtained by oxidation of ethylene, and the carbon dioxide feed is a by-product of the oxidation of ethylene.

Figure 1:
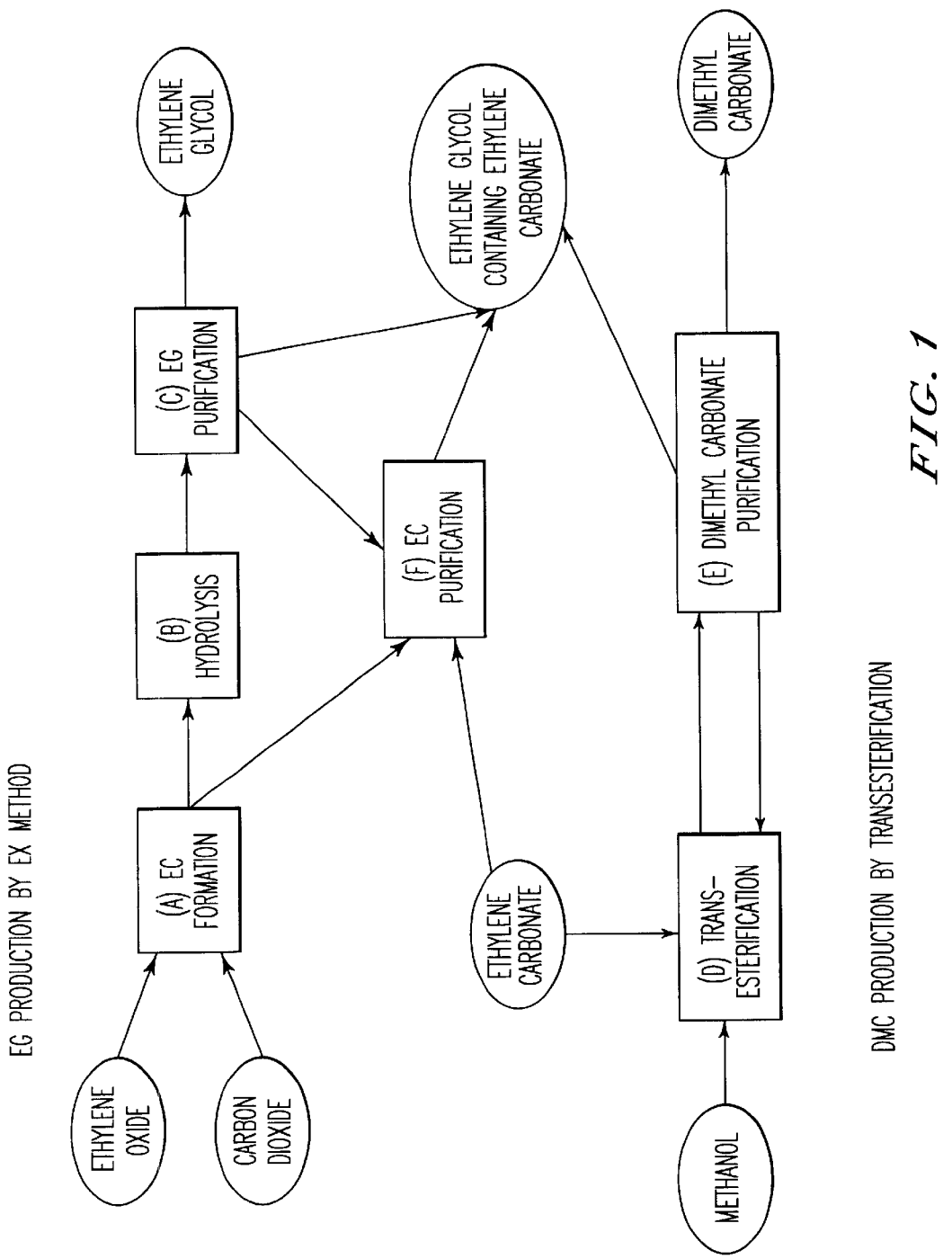
FIG. 1 is a block flow diagram of an embodiment of the present invention.

Now, the present invention is described in detail by referring to the block flow diagram of an example wherein the hydroxyl group-containing compound is methanol, and the carbonated ester is dimethyl carbonate, shown in FIG. (1) Steps (a) to (c): process for producing EG by the EC method

Step (a) (EC formation)

The step (a) comprises the reaction of ethylene oxide and carbon dioxide are reacted usually in the presence of a catalyst and gives a reaction solution containing ethylene carbonate.

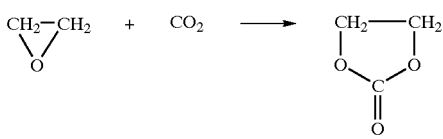

The starting material, ethylene oxide, is usually obtained by partial oxidation of ethylene. The carbon dioxide could be obtained by burning hydrocarbons, but it is economical to use the by-product of the combustion of ethylene for production of ethylene oxide.

As the catalyst for this reaction, a phosphonium salt is preferable for its high activity and recyclability. It is preferable to use an alkali metal carbonate as a promoter. Besides, introduction of water in the system is preferable because addition of water accelerates the reaction.

The type of the reactor for this reaction is not particularly limited, but it is efficient to use a bubble column reactor, which introduces ethylene oxide, carbon dioxide, water and a catalyst from the bottom and discharges the resulting reaction solution containing ethylene carbonate and unreacted carbon dioxide from the top.

The reaction is usually conducted at a temperature of from 70 to 100° C., preferably from 100 to 170° C., at a pressure of from 5 to 50 kg/cm$^2$·G (gauge pressure), preferably from 10 to 30 kg/cm$^2$·G. The feed ratios of carbon dioxide and water to ethylene oxide (molar ratios) are usually from 0.1 to 5 and from 0.1 to 10, respectively, preferably from 0.5 to 3 and from 0.5 to 5, respectively.

Because the reaction involved in this step is exothermic, it is preferred to control the reaction temperature by an external circulating cooling system by which part of the reaction solution is drawn out, cooled by a heat exchanger and then returned to the system.

The reaction mixture obtained in the step (a) usually contains not only ethylene carbonate but also unreacted carbon dioxide, water, ethylene glycol, the catalyst and a trace of unreacted ethylene oxide. Because ethylene oxide is a noxious gas and can lead to formation of by-products such as diethylene glycol in the hydrolysis step, it is preferred to promote the reaction until the ethylene oxide content becomes substantially zero (until the conversion becomes almost 100%) by using an additional tubular reactor or the like.

Step (b) (hydrolysis)

In the step (b), liquid containing ethylene carbonate such as the reaction mixture containing ethylene carbonate obtained in the step (a) and the remainder obtained in the after-mentioned step (f) after separation of ethylene carbonate, and optionally the remainder left behind the separation of the carbonate ester in the after-mentioned step (e) is treated with water to form ethylene glycol in accordance with the following formula.

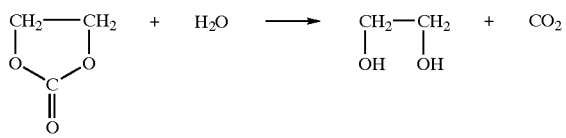

The hydrolysis is usually conducted at from 100 to 180° C. because though high temperatures are kinetically advantageous, too high temperatures can cause degradation of the catalyst for EC formation and deteriorate the quality of ethylene glycol, causing discoloration or the like. Lower pressure is favorable to promote the reaction, but pressures much lower than the saturated vapor pressure of the reaction solution retard the reaction or cause the loss of the product because the reaction solution would boil, vaporizing water or ethylene glycol. The reaction pressure is usually within the range of from atmospheric pressure to 20 kg/cm$^2$·G and selected so that the reaction solution does not boil. It is also preferred to divide this step into several stages and elevate the temperature or lower the pressure gradually as the hydrolysis proceeds in order to promote the reaction.

This step gives an ethylene glycol aqueous solution containing the catalyst for EC formation and liberates carbon dioxide as a volatile component in the gas phase.

Step (c) (EG purification)

The step (c) purifies and isolates ethylene glycol as a product from the ethylene glycol aqueous solution obtained in the step (b).

This step usually entails distillation, preferably combination of dehydration distillation for removal of water from the top and EG rectification for separation of EG from high-boiling components such as diethylene glycol and the catalyst.

The high-boiling remainders left in the EG purification step can be returned to the step (a) for reuse as a catalyst solution, if necessary, after partly purged from the system. Especially, it is possible and preferred to recycle the catalyst solution more efficiently by dividing the EG rectification into two steps and purging only the high-boiling components free from the catalyst. (2) Steps (d) and (e): process for producing a carbonate ester Step (d) (transesterification)

The step (d) comprises the transesterification of ethylene carbonate and methanol in the presence of a catalyst and gives dimethyl carbonate and ethylene glycol in accordance with the following formula.

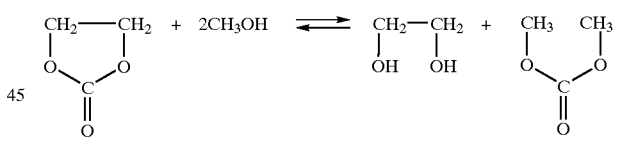

As the transesterification catalyst used in the reaction, ordinary catalysts for transesterification of carbonates may be used without any particular restriction. Specific examples include homogeneous catalysts such as amines represented by triethylamine, alkali metals represented by sodium, alkali metal compounds represented by sodium chloroacetate and sodium methylate and thallium compounds and heterogeneous catalysts such as functional group-modified ion exchange resins, amorphous silica impregnated with alkali metal or alkaline earth metal silicates, ammonium-exchanged zeolite Y and the double oxide of cobalt and nickel.

In the present invention, as the hydroxyl group-containing compound, in addition to methanol mentioned as a specific example, a phenol such as phenol, bisphenol or an alkylphenol, a monohydric alcohol such as ethanol, isopropanol or cyclohexanol, a dihydric alcohol such as propanediol, butanediol or hexanediol or a polyhydric alcohol such as glycerin may be used without any particular restriction. Among them, preferred is a monohydric or dihydric alcohol, especially methanol, which gives the carbonate ester of great industrial significance.

As to the reaction conditions for the transesterification, the reaction temperature is usually from 50 to 180° C., and the molar feed ratio of a hydroxyl group-containing compound such as methanol to ethylene carbonate is usually from 2 to 20. If the molar ratio is less than 2, the conversion in the transesterification is low due to the shortage of the hydroxyl group-containing compound, and if the hydroxyl group-containing compound is used at a ratio higher than 20, considerable part of the starting materials remain unreacted in the system, increasing the energy necessary for heating and cooling and the load of recycling on the facilities.

As mentioned above, the transesterification is an equilibratory reaction, and therefore unreacted ethylene carbonate is always present in the reaction system. Namely, the product solution obtained in the step (d) contains not only dimethyl carbonate and ethylene glycol as the target products but also ethylene carbonate and methanol as the starting materials.

Step (e) (carbonate purification)

In the step (e), methanol and then dimethyl carbonate are separated from the reaction solution obtained in the step (d), if necessary after removal and recovery of the transesterification catalyst, and the remainder containing ethylene carbonate and ethylene glycol is recovered.

This step involves various techniques such as distillation. The remainder is usually supplied to the after-mentioned step (f) (EC purification), but could be subjected to fractional distillation so that ethylene glycol containing ethylene carbonate is withdrawn from the top and supplied to the above-mentioned step (b), skipping the step (f), while the remainder mainly containing ethylene carbonate is withdrawn from the bottom and returned to the step (d) (transesterification step).

(3) Step (f): EC purification process

The present invention combines production of ethylene glycol by the EC method and production of dimethyl carbonate by the transesterification method with intervention by the step (f).

Namely, the step (f) deals with at least part of the reaction solution obtained in the step (a) and the remainder left behind the recovery of methanol and dimethylcarbonate in the step (e) or deals with the reaction solution obtained in the step (a) only, and separates ethylene carbonate by distillation while feeding the remainder left behind the separation of EC to the step (b).

Because ethylene carbonate and ethylene glycol are azeotropic with each other as mentioned above, sufficient separation of the two is necessary to produce dimethyl carbonate entails, though not to produce ethylene glycol. Such separation requires, for example, a distillation column with a large theoretical plate number or a multiple distillation column complex. However, in the present invention, as long as ethylene carbonate is obtained in an amount necessary for the reaction in the step (d), the remaining ethylene carbonate may be hydrolyzed after supplied to the step (b) in the form of a mixture of ethylene carbonate and ethylene glycol. Further, this step allows the unreacted ethylene carbonate remaining after the formation of the carbonate ester by the equilibratory reaction to be recovered efficiently and reused in the step (d) and supplied to the hydrolysis step (b) for production of ethylene glycol and thus enables efficient facility operation.

As a preferable equipment for this step, for example, a distillation equipment comprising two distillation columns. The first distillation column distils out, from the top, water, ethylene glycol and azeotropic ethylene carbonate, which are then fed to the step (b), and discharges the high-boiling fraction mainly composed of ethylene carbonate from the bottom. The second distillation column distils out purified ethylene carbonate as a top fraction from the discharge, and discharges the high-boiling fraction from the bottom.

In the distillation, it is preferred to control the retention time in the first distillation column, because ethylene glycol as a by-product can be left in the heavy fraction, and the amount of diethylene glycol accompanying ethylene carbonate in the top fraction can be reduced.

The above-mentioned process of the present invention combines production of ethylene glycol and production of a carbonate ester efficiently.

Now, the present invention will be described in further detail with reference to Examples. However, it should be understood that the present invention is by no means restricted to such specific Examples.

Figure 2:
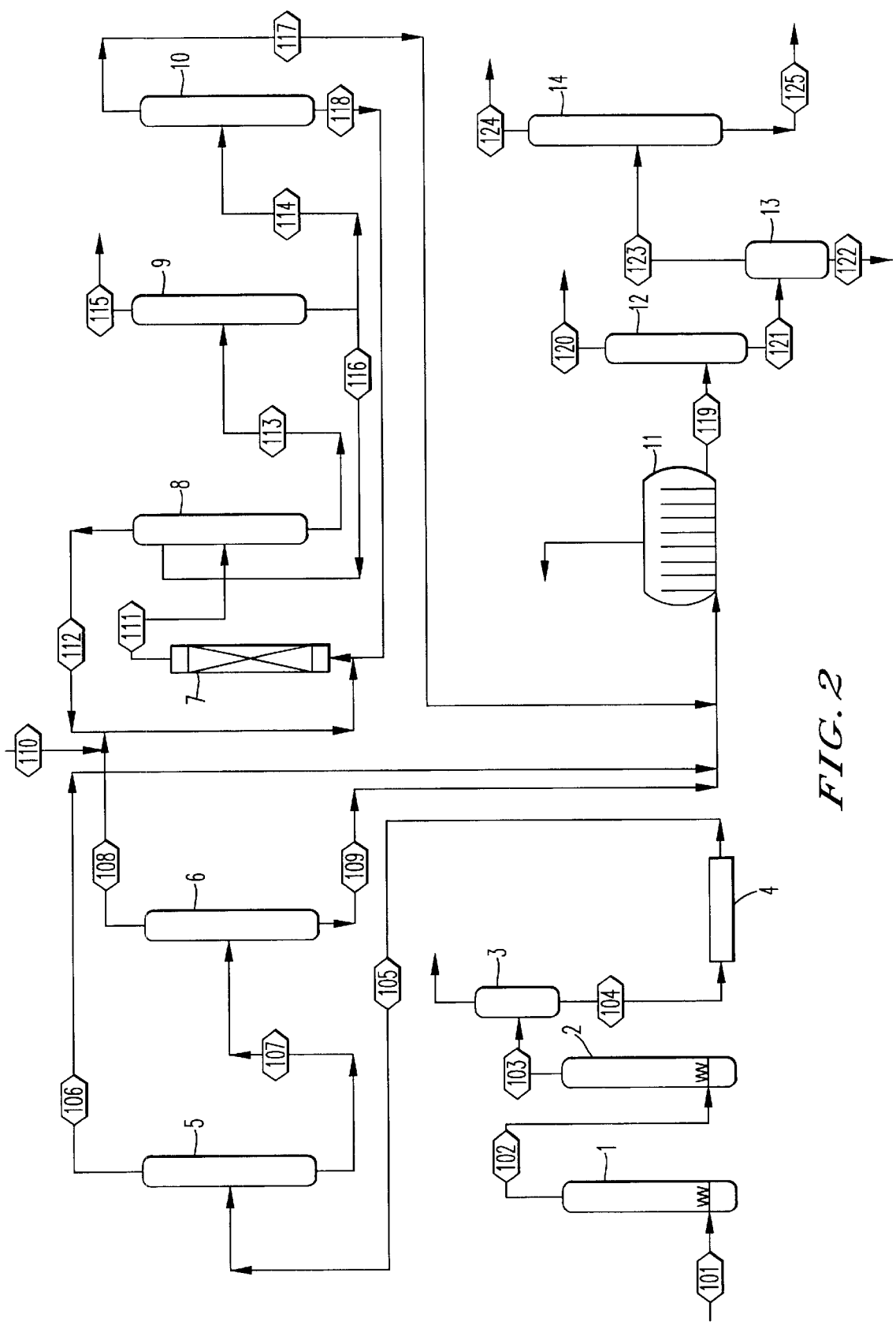
FIG. 2 is a process flow diagram of an example of the present invention.

One embodiment of the present invention will be described with reference to FIG. 2. For the sake of explanation, production of ethylene glycol and production of a carbonate ester are explained in parallel.

(1) Step (a) (EC formation)

EC formation was carried out in two bubble column reactors (1 and 2) of 20 cm in diameter and 230 cm in height connected in series. 65 kg/h of ethylene oxide and 140 kg/h of carbon dioxide as the starting materials, 47 kg/h of water and a catalyst solution of 9.3 kg/h of tributylmethylphosphonium iodide and 0.373 kg/h of potassium carbonate dissolved in 16.5 kg/h of ethylene glycol were fed through a line 101. The reaction was carried out at 110° C. at a pressure of 20 kg/cm$^2$·G.

From the gas-liquid mixture withdrawn through a line 103, the gas phase was separated in a gas-liquid separator (3), and the resulting reaction solution was fed to a tubular reactor (4) of 6 cm in diameter and 200 cm in length maintained at 110° C. and 20 kg/cm$^2$·G through a line 104. The reaction was carried out until the amount of residual ethylene oxide became lower than the lower detection limit (10 ppm) of gas chromatographic analysis. The reaction solution in the line 105 comprised 51 wt % (% denotes wt % hereafter) of ethylene carbonate, 21% of water, 22% of ethylene glycol and 6% of the balance including the catalyst and heavy substances.

(2) Step (f) (EC purification)

The entire reaction solution obtained in the step (a) was fed to a first distillation column (5) through a line 105. The top pressure of the column was 30 mmHg (absolute pressure, hereinafter), the top temperature was 36° C., and the bottom temperature was 145° C.

70.3 kg/h of a liquid mixture containing water, ethylene glycol and a slight amount of azeotropically accompanying ethylene carbonate was withdrawn from the top and fed to a hydrolysis reactor (11) through a line 106 while 98.9 kg/h of a liquid containing a high concentration of ethylene carbonate was withdrawn from the bottom and fed to the second distillation column (6).

The top pressure of the second distillation column (6) was 30 mmHg, the top temperature was 141° C., and the bottom temperature was 148.8° C. 58.7 kg/h of ethylene carbonate was obtained from the top with a purity of at least 99.9%. 25.5 kg/h of the liquid at the bottom was fed to the hydrolysis reactor (11) through a line 109.

(3) Step (d) (transesterification)

The purified ethylene carbonate withdrawn from the second distillation column (6) was fed to a transesterification reactor (7) through a line 108. At the same time, 38.5 kg/h of fresh methanol and 83.2 kg/h of the recovered methanol solution mainly composed of methanol withdrawn from a methanol recovery column (8) and 67.2 kg/h of recycled ethylene carbonate recovered from an ethylene carbonate recovery column were fed through a line 110, a line 112 and a line 118, correspondingly. The reaction was carried out in a jacketed tubular reactor of 28 cm in diameter and 200 cm in length loaded with a cobalt-yttrium double oxide catalyst prepared in accordance with JP-A-8-176071 (Example 1) as the transesterification reactor while the inner temperature was maintained at 140° C. by heating the reactor with the jacket from the outside. 247 kg/h of the reaction solution was withdrawn through a line 111. The reaction solution at the outlet of the reactor comprised 29.5% of ethylene carbonate, 15.2% of ethylene glycol, 30.4% of methanol and 24.9% of dimethyl carbonate.

(4) Step (e) (purification of carbonate ester)

The esterification reaction solution was fed to the ethanol recovery column (8) through a line 111. Part of the bottom fraction in the dimethyl carbonate recovery column (9) was fed to the methanol recovery column (8) through a line 116 at a rate of 400 kg/h. The operation was done at a top pressure of 760 mmHg, a top temperature of 64° C. and a bottom temperature of 178° C. 83.2 kg/h of a liquid mixture comprising 90% of methanol and 10% of dimethyl carbonate was withdrawn from the top, and 564 kg/h of the bottom fraction was fed to the dimethyl carbonate recovery column (9) through a line 113.

The dimethyl carbonate recovery column (9) was operated at a top pressure of 200 mmHg, a top temperature of 53.2° C. and a bottom temperature of 166° C., and 54 kg/h of dimethyl carbonate with a purity of at least 99.99% was withdrawn through a line 115 at the top. Part of the bottom fraction was returned to the methanol recovery column (8), and the remainder was fed to an ethylene carbonate recovery column (10) through a line 114 at a rate of 110 kg/h.

The ethylene carbonate recovery column (10) was operated at a top pressure of 60 mmHg, a top temperature of 127.7° C. and a bottom temperature of 157.7° C., and ethylene glycol formed by the transesterification was withdrawn from the top together with azeotropically accompanying ethylene carbonate and supplied to the hydrolysis step through a line 117, while ethylene carbonate at the bottom was returned to the transesterification reactor (7) through a line 118.

(5) Step (b) (hydrolysis)

The hydrolysis reactor (11) was fed through lines 106, 109 and 117 and operated at a reaction temperature of 150° C. and a pressure of 1.8 kg/cm$^2$·G. As the hydrolysis reactor, a reaction vessel of 32 cm in diameter and 3 m in length having a partition inside for prevention of back mixing was used. The reaction temperature was kept constant by heating by using steam from the outside.

The ethylene carbonate concentration at the outlet line 119 was lower than the lower detection limit (10 ppm) of gas chromatographic analysis.

(6) Step (c) (purification of ethylene glycol)

A dehydration distillation column was fed through a line 119 and operated at a top pressure of 80 mmHg and a bottom temperature of 140° C., while water was removed from the top through a line 120.

Then, the bottom fraction was fed to a catalyst separator (13) operated at a pressure of 62 mmHg and a temperature of 140° C. through a line 121, and crude ethylene glycol freed from the catalyst and high-boiling substances was withdrawn through a line 123.

The crude ethylene glycol was purified in an ethylene glycol purification column (14) operated at a top pressure of 52 mmHg and a bottom temperature of 160° C., and 96.5 kg/h of purified ethylene glycol was withdrawn through a line 124 at the top.

The process of the present invention which combines production of ethylene glycol and production of a carbonate ester has the following effects and therefore is of high utility value from the industrial aspect and environmentally advantageous:

(1) acceleration of the reaction of ethylene oxide and carbon dioxide for production of ethylene carbonate by addition of water is available to production of EC which is to be transesterified to a carbonate ester.

(2) the azeotropic mixture of ethylene carbonate and ethylene glycol can be treated in the hydrolysis step, and advanced separation and purification facilities are not necessary; and (3) since the carbon dioxide used in production of ethylene carbonate is immobilized in the carbonate ester, the leakage of carbon dioxide into the environment can be reduced.

The entire disclosure of Japanese Patent Application No. 2000-009865 filed on Jan. 19, 2000 including specification, claims, drawings and summary are incorporated herein by reference in its entirety.

What is claimed is:

1. A process for simultaneously producing ethylene glycol and a carbonate ester comprising the following steps (a) to (c) for production of ethylene glycol, the following steps (d) and (e) for production of a carbonate ester and the following step (f) for purification of ethylene carbonate, wherein the step (f) intervenes to combine production of ethylene glycol and production of the carbonate ester:

(a) an EC formation step of reacting ethylene oxide and carbon dioxide to form a reaction solution containing ethylene carbonate, (b) a hydrolysis step of reacting the solution containing ethylene carbonate with water to give an aqueous solution containing ethylene glycol, (c) an EG purification step of purifying and collecting ethylene glycol from an aqueous solution containing ethylene glycol obtained mainly in the step (b), (d) a transesterification step of transesterifying ethylene carbonate and a hydroxyl group-containing compound to form the corresponding carbonate ester and ethylene glycol, (e) a carbonate purification step of separating the carbonate ester from the solution obtained in the step (d), and (f) an EC purification step of separating ethylene carbonate by distillation from at least part of the reaction solution obtained in the step (a) and the remainder left behind the separation of the carbonate ester in step (e), feeding the ethylene carbonate to the step (d) and feeding the remainder to the step (b).

2. The process for simultaneously producing ethylene glycol and a carbonate ester according to claim 1, wherein ethylene glycol containing ethylene carbonate is separated from the remainder left behind the separation of the carbonate ester in step (e) as the top fraction and fed to the step (b) without passing the step (f), and the remainder as the bottom fraction is returned to the step (d).

3. The process for simultaneously producing ethylene glycol and a carbonate ester according to claim 1, wherein the hydroxyl group-containing compound is a monohydric or dihydric alcohol.

4. The process for simultaneously producing ethylene glycol and a carbonate ester according to claim 1, wherein the hydroxyl group-containing compound is methanol, and the carbonate ester is dimethyl carbonate.

5. The process for simultaneously producing ethylene glycol and a carbonate ester according to claim 1, wherein the ethylene oxide feed to the step (a) is obtained by oxidation of ethylene, and the carbon dioxide feed is a by-product of the oxidation of ethylene.

* * * * *